US012038427B2

United States Patent
Dutta et al.

(10) Patent No.: US 12,038,427 B2
(45) Date of Patent: Jul. 16, 2024

(54) APPARATUS AND METHOD FOR MULTIMODAL SENSING AND MONITORING OF PERISHABLE COMMODITIES

(71) Applicant: Tata Consultancy Services Limited, Mumbai (IN)

(72) Inventors: Jayita Dutta, Pune (IN); Parijat Deshpande, Kolkata (IN); Beena Rai, Pune (IN)

(73) Assignee: Tata Consultancy Services Limited, Mumbai (IN)

( * ) Notice: Subject to any disclaimer, the term of this patent is extended or adjusted under 35 U.S.C. 154(b) by 541 days.

(21) Appl. No.: 17/296,967

(22) PCT Filed: Oct. 25, 2019

(86) PCT No.: PCT/IN2019/050789
§ 371 (c)(1),
(2) Date: May 25, 2021

(87) PCT Pub. No.: WO2020/089929
PCT Pub. Date: May 7, 2020

(65) Prior Publication Data
US 2021/0405009 A1    Dec. 30, 2021

(30) Foreign Application Priority Data

Oct. 29, 2018   (IN) .............. 201821040783

(51) Int. Cl.
*G01N 33/02*       (2006.01)
*G05B 13/02*      (2006.01)
(Continued)

(52) U.S. Cl.
CPC .......... *G01N 33/02* (2013.01); *G05B 13/029* (2013.01); *G06Q 10/087* (2013.01);
(Continued)

(58) Field of Classification Search
CPC .......... G06T 2207/30128; G06T 2207/20081; G01N 33/02; G01N 33/025;
(Continued)

(56) References Cited

U.S. PATENT DOCUMENTS 9,824,298 B1 *  11/2017  Krishnan Gorumkonda .............. G06V 10/255
11,448,632 B2 *  9/2022  Velez ...................... G06Q 10/04
(Continued)

OTHER PUBLICATIONS

Mustafa, Fatima et al., "Chemical and Biological Sensors for Food-Quality Monitoring and Smart Packaging", Sensors Application in Food Analysis and Detection, Oct. 2018, vol. 7 (10), MDPI, https://www.mdpi.com/2304-8158/7/10/168.
(Continued)

*Primary Examiner* — Yoshihisa Ishizuka
*Assistant Examiner* — Carter W Ferrell
(74) *Attorney, Agent, or Firm* — Finnegan, Henderson, Farabow, Garrett & Dunner, LLP

(57) ABSTRACT

Health of perishable commodities such as eatables deteriorate over time. State of art systems for health monitoring of perishable commodities rely on measurement of limited parameters and also fail to consider effect of environment on the health of the perishable commodities. Disclosed herein is an apparatus and method for multimodal sensing and monitoring of perishable commodities. The apparatus allows to change environment within a closed chamber in which the perishable commodity being monitored is kept, and in turn allows to generate health data in different environment settings. This data is used to generate a health model. Data collected in real-time are processed with the health model to establish a correlation with at least one image, wherein each of such images in the health model represents certain health state. Based on the established correlation, health of the perishable commodity is determined.

12 Claims, 6 Drawing Sheets

(51) Int. Cl.
  *G06Q 10/087* (2023.01)
  *G06T 7/00* (2017.01)
(52) U.S. Cl.
  CPC .......... *G06T 7/0004* (2013.01); *G01N 33/025* (2013.01); *G06T 2207/20081* (2013.01); *G06T 2207/20084* (2013.01); *G06T 2207/30128* (2013.01)
(58) Field of Classification Search
  CPC ......... G01N 2021/8466; G06Q 10/087; G06Q 10/0832; G06K 19/0717; G06V 20/68; G06V 10/82; G06V 10/764
  See application file for complete search history.

(56) References Cited

U.S. PATENT DOCUMENTS

| | | |
|---|---|---|
| 2015/0082815 A1 | 3/2015 | Bell |
| 2016/0196527 A1 | 7/2016 | Bose et al. |
| 2019/0285603 A1* | 9/2019 | Velez ...................... G06Q 10/04 |
| 2020/0005230 A1* | 1/2020 | Brooks .................. A23N 15/06 |
| 2020/0097776 A1* | 3/2020 | Kim ........................... G06T 7/70 |
| 2020/0122926 A1* | 4/2020 | Bohling ............... B65G 1/1373 |
| 2020/0275671 A1* | 9/2020 | Holm .................... A23L 3/3445 |
| 2020/0311663 A1* | 10/2020 | Chopko ................. G06Q 10/08 |

OTHER PUBLICATIONS

Popa, Alexandru et al., "An Intelligent IoT-Based Food Quality Monitoring Approach Using Low-Cost Sensors", Symmetry, 2019, vol. 11 (3), MDPI, https://www.mdpi.com/2073-8994/11/3/374/pdf.
International Search Report mailed Jun. 10, 2020, in International Application No. PCT/IN2019/050789; 1 page.

* cited by examiner

APPARATUS AND METHOD FOR MULTIMODAL SENSING AND MONITORING OF PERISHABLE COMMODITIES

PRIORITY CLAIM

The present application is a U.S. National Stage Filing under 35 U.S.C. § 371 and claims priority from International Application No. PCT/IN2019/050789 filed on Oct. 25, 2019, which application claims priority under 35 U.S.C. § 119 from India Application No. 201821040783, filed on Oct. 29, 2018. The entire contents of the aforementioned applications are incorporated herein by reference.

TECHNICAL FIELD

This disclosure relates generally to monitoring systems, and more particularly to a method and apparatus for monitoring of perishable commodities.

BACKGROUND

In various fields of application, perishable commodities are used. Food industry is an example. In the food industry, raw materials used for preparing food, as well as final output of cooking (i.e. food) are both perishable commodities i.e. having specific life span after which decaying of the raw materials/food begins. The raw materials as well as the food may have to be kept in a production/storage environment for certain time, and also may have to be transported from one location to another. It is possible that during storage, production, or transportation, the process of decaying/quality degradation starts.

The inventors here have recognized several technical problems with such conventional systems, as explained below. As it is important to identify such instances of food (or other such perishable commodities) decaying/degradation, certain sensing systems are used for continuous monitoring purpose. One of the disadvantages of the existing systems being used for sensing perishable commodities is that they rely on sensing and processing a single parameter such as one of odour, visual observation, pictorial changes, emitted gasses, by chemical changes, and so on. However, the effect/significance of such characteristics may vary from one perishable commodity to another. Also, in certain circumstances, sensing only one of the aforementioned parameters may not give a clear indication of quality of a perishable commodity being monitored. Moreover the existing sensing and monitoring systems mainly facilitate qualitative analysis but do not provide any quantitative measurement for the degree of freshness of the perishable items.

SUMMARY

Embodiments of the present disclosure present technological improvements as solutions to one or more of the above-mentioned technical problems recognized by the inventors in conventional systems. For example, in one embodiment, a processor implemented method for monitoring health of a perishable commodity is provided. Initially, information pertaining to a distinct environmental setting is collect from a user as input, and the environment within the closed chamber is set to the distinct environmental setting by varying value of the one or more environmental parameters. Further, value of one or more health parameters corresponding to the perishable commodity being monitored is collected, using at least one of the plurality of sensors. Further, a correlation between the collected value of one or more health parameters with at least one time series image representing a health state is established, by comparing the collected value of one or more health parameters with a pre-trained health model, the pre-trained health model trained on sensor and image data indicating change in health of a plurality of perishable commodities with time under plurality of environmental settings. Further, health of the perishable commodity is determined based on the established correlation.

In another aspect, an apparatus for monitoring health of a perishable commodity is provided. The apparatus comprises a housing with closed walls, a sensor suit comprising a plurality of sensors, wherein the sensor suite is attached internally to the housing, a support structure for keeping the perishable commodity within the housing, wherein the perishable commodity is kept in proximity of the plurality of sensors, one or more hardware processors, one or more communication interfaces, and one or more memory storing a plurality of instructions. The plurality of instructions when executed cause the one or more hardware processors to collect information pertaining to a distinct environmental setting from a user and set the environment within the closed chamber to the distinct environmental setting by varying value of the one or more environmental parameters. Further, value of one or more health parameters corresponding to the perishable commodity being monitored is collected, using at least one of the plurality of sensors. Further, a correlation between the collected value of one or more health parameters with at least one time series image representing a health state is established, by comparing the collected value of one or more health parameters with a, pre-trained health model, the pre-trained health model trained on sensor and image data indicating change in health of a plurality of perishable commodities with time under plurality of environmental settings. Further health of the perishable commodity is determined based on the established correlation.

In yet another aspect, a non-transitory computer readable medium for monitoring health of a perishable commodity is provided. Initially, information pertaining to a distinct environmental setting is collect from a user as input, and the environment within the closed chamber is set to the distinct environmental setting by varying value of the one or more environmental parameters. Further, value of one or more health parameters corresponding to the perishable commodity being monitored is collected, using at least one of the plurality of sensors. Further, a correlation between the collected value of one or more health parameters with at least one time series image representing a health state is established, by comparing the collected value of one or more health parameters with a pre-trained health model, the pre-trained health model trained on sensor and image data indicating change in health of a plurality of perishable commodities with time under plurality of environmental settings. Further, health of the perishable commodity is determined based on the established correlation.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this disclosure, illustrate exemplary embodiments and, together with the description, serve to explain the disclosed principles.

DETAILED DESCRIPTION

Exemplary embodiments are described with reference to the accompanying drawings. In the figures, the left-most digit(s) of a reference number identifies the figure in which the reference number first appears. Wherever convenient, the same reference numbers are used throughout the drawings to refer to the same or like parts. While examples and features of disclosed principles are described herein, modifications, adaptations, and other implementations are possible without departing from the scope of the disclosed embodiments. It is intended that the following detailed description be considered as exemplary only, with the true scope being indicated by the following claims.

Figure 1:
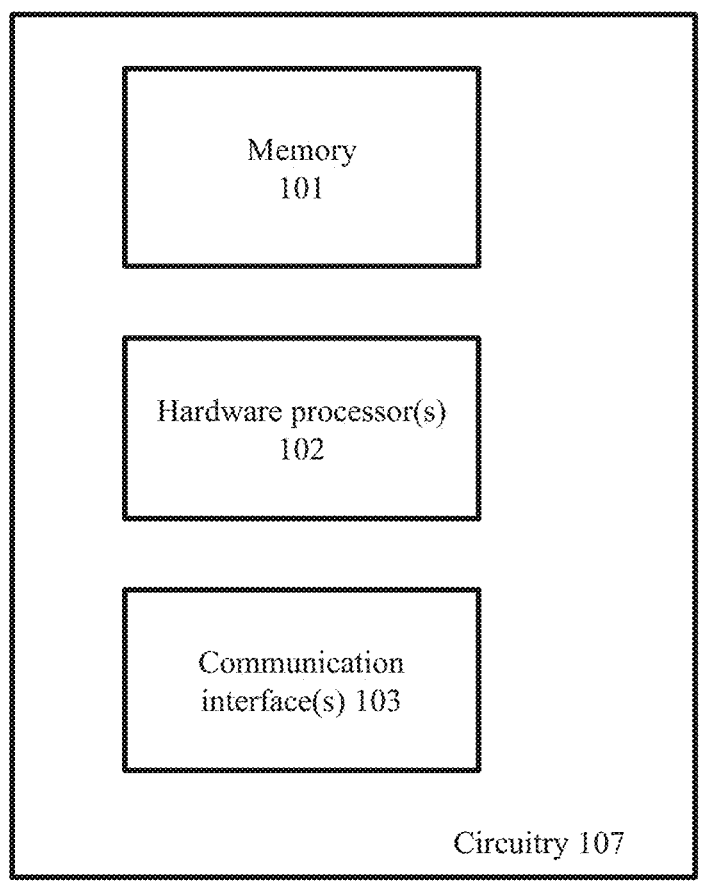
FIG. 1 illustrates an exemplary block diagram illustrating a circuitry of an apparatus for monitoring health of perishable commodities, according to some embodiments of the present disclosure.

FIG. 1 illustrates an exemplary block diagram illustrating a circuitry 107 of an apparatus 100 for sensing perishable commodities, according to some embodiments of the present disclosure. The circuitry 107 includes one or more memories 101, one or more hardware processors 102, and one or more communication interfaces 103. The circuitry 107 is one of the components of the apparatus 100 configured within the housing and communicably coupled with a sensor suite 104 to determine the health of the perishable commodity. In addition to the circuitry 107, the apparatus 100 includes the sensor suite 104, a support structure 105, and an environment controller 106. The memory module(s) 101 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 101 is configured to store any data associated with the health estimation of the perishable commodities, permanently or temporarily, and can be further configured to provide authorized access to the data.

The one or more hardware processors 102 can be implemented as one or more microprocessors, microcomputers, microcontrollers, digital signal processors, central processing units, state machines, graphics controllers, logic circuitries, and/or any devices that manipulate signals based on operational instructions. Among other capabilities, the processor(s) are configured to fetch and execute computer-readable instructions stored in the memory.

The communication interface(s) 103 can include a variety of software and hardware interfaces, for example, a web interface, a graphical user interface, and the like and can facilitate multiple communications within a wide variety of networks N/W and protocol types, including wired networks, for example, LAN, cable, etc., and wireless networks, such as WLAN, cellular, or satellite. In an embodiment, the communication interface(s) 103 can include one or more ports for connecting the apparatus to one or more other apparatuses 101 or any other suitable devices for data transfer or collaboration and so on.

Figure 2:
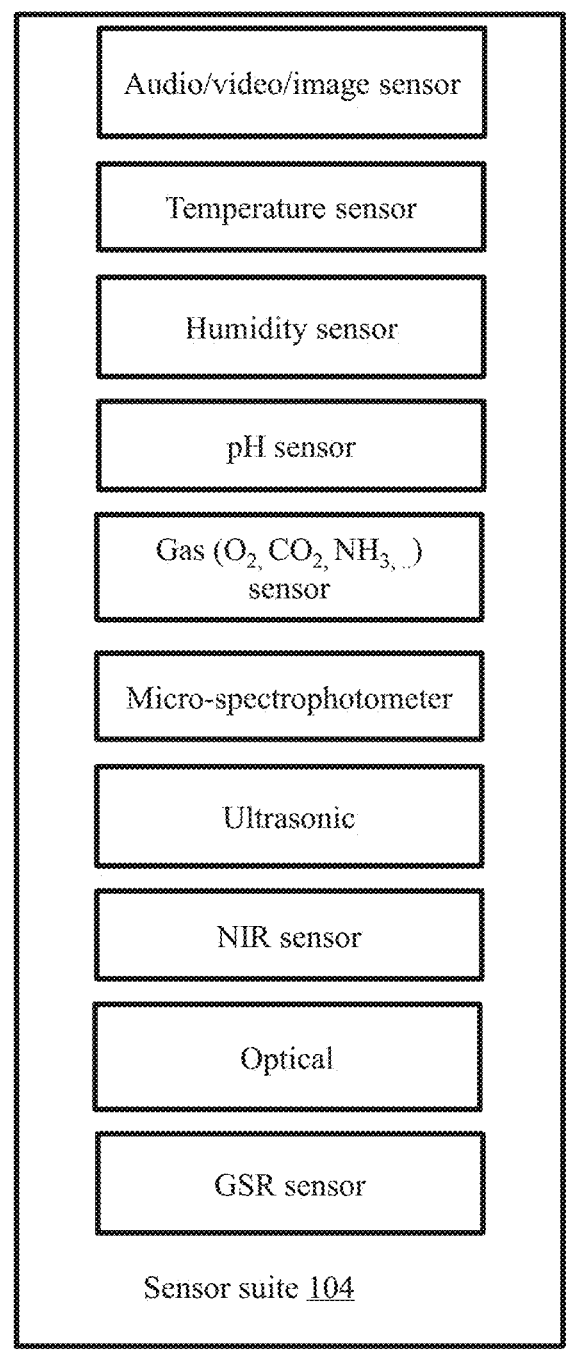
FIG. 2 is a block diagram depicting components of sensor suite of the apparatus of FIG. 1, according to some embodiments of the present disclosure.

The sensor suite 104 is configured to perform sensing and monitoring of one or more perishable commodities periodically. During monitoring of the one or more perishable commodities, the sensor suite 104 collects, using one or more appropriate sensors, data pertaining to one or more features of the perishable commodity being monitored. A few examples of different types of sensors and other components being used by the sensor suite 104 are given in FIG. 2. As in FIG. 2, the sensor suite 104 includes mutually exclusive sensors such as an audio/video/image sensor, a temperature sensor, a humidity sensor, a pH sensor, a gas sensor, a microspectrophotometer, ultrasonic sensor, NIR, optical, and a GSR. The sensor suite 104 may include an on-board memory for data storage. The ultrasonic sensor can be used to measure change in composition of perishable commodity non-invasively by using ultrasonic waves, the NIR sensor with microspectrophotometer is used for getting spectra of sub-micron levels in the perishable commodity, the GSR sensor may be used to observe minute and delicate changes with respect to skin resistance of the perishable commodity (for example, a food item), which marks the beginning of degradation and which cannot be measured otherwise. These individual Commercial Off The Shelf (COTS) sensors are suitably modified to meet the requirements, e.g. GSR sensor electrodes are modified to allow sensing of fresh fruits. The sensor module 104 can be interfaced with a variety of computing systems, such as laptop computers, notebooks, hand-held devices, workstations, mainframe computers, servers, a network cloud and the like.

The perishable commodity being monitored is kept on the support structure 105 such that the perishable commodity is kept in proximity of a plurality of sensors in the sensor suite 104. Apart from time, a factor that affects deterioration of health of the perishable commodities is environmental condition in which the perishable commodity is placed. For example, a fruit deteriorates faster when kept at high temperature. In order to assess deterioration of the perishable commodity under different environmental conditions, the environment controller 106 is used. The environment controller 106 collects information pertaining to a distinct environmental setting as input, processes the collected input, and determines value of one or more environmental factors/parameters so as to achieve the distinct environmental setting. For example, a user may specify the distinct environmental setting in terms of specific values of temperature and atmospheric pressure to be maintained within the housing. After determining value all the environmental parameter(s) to be changed, the environment controller 106 sends instructions to appropriate components to change the value accordingly. In the aforementioned scenario, the environment controller 106 sets values of the pressure and temperature to the distinct values. In various embodiments appropriate measures for changing values of the parameters may be internally or externally connected to the apparatus. For example, an air-conditioning component used for varying the temperature inside the housing maybe internally or externally connected to the housing, through appropriate connecting options provided on the housing. In an embodiment, the housing has a plurality of slots for supporting connection of various such components and/or the sensors associated with the sensor suite 104.

After setting the environment inside the housing to the distinct setting, value of one or more health parameters are measured/collected using appropriate sensor(s) in the sensor suite 104 by the system 100. In an embodiment, one or more sensors from the plurality of sensors in the sensor suite 104 are selected automatically, based on the type of commodity being monitored, wherein information pertaining to type of parameters to be measured and corresponding sensors for different types of perishable commodities are pre-configured or dynamically configured with the memory 101. The apparatus may determine the type of perishable commodity to be monitored, automatically based on one or more sensor inputs, or based on a manual input, or a combination thereof. The system 100 may do a pre-processing of the collected data for the purpose of conditioning the data for further processing. Components such as but not limited to an anti-aliasing filter, a pre-amplifier, a variable frequency control (V/F), and a counter circuit, and so on maybe used for pre-processing of the collected data. For example, sensed raw signal from the sensors may be fed to the isolation circuit in to remove induced noise from the sensor signal(s), prevent ground looping in the communication network and provide proper isolation between the sensor signals. Further, signal conditioning may be performed which involves filtering of unwanted frequencies, followed by voltage amplification by the preamplifier for further digitization by a data acquisition equipment and finally for generating analog to digital output data streams to be further processed for determining health of the perishable commodity being monitored. The sensor data collected by setting the environmental setting to the distinct environmental setting helps in determining characteristics of the perishable commodity under different environmental conditions. This data can be used to train a health model and can also be used by a user to simulate different environmental conditions to determine impact of the same on the health of the perishable commodity.

The system 100 stores the health model in the memory 101, wherein the health model is a combination of a plurality of machine learning algorithms. In an embodiment, the health model includes at least one Convolution Neural network (CNN) model. The at least one CNN model is trained with a plurality of time series images to extract a plurality of vector representations which represent degradation in a plurality of perishable commodities, further wherein the vector representation of the time series images are annotated as representing a degree of freshness level. Different images used for training CNN model may represent different health states of each of the perishable commodities being monitored by the apparatus 100. Additionally or alternatively, the health model may also comprise at least one Support Vector Regression (SVR) model. The at least one SVR model is trained on a plurality of features extracted from a plurality of time series sensory data collected from the plurality of perishable commodities, further wherein the time series sensory data are annotated as representing a degree of freshness level. The term 'degree of freshness level' may indicate different stages/states with respect to freshness of the perishable commodity. For example, if the perishable commodity being monitored is a fruit, different degree of freshness levels indicate different ripening stages of the fruit such as not ripen, medium ripen, fully ripen and so on. In an embodiment, the health model may include one or more of other types of machine learning models as well, apart from the at least one CNN model and the at least one SVR model.

The hardware processor(s) 102 compares the collected value of health parameters with the health model and establishes a correlation between the collected value of health parameters and at least one time series image representing a health state. In an embodiment, the health model is unique to each type of perishable commodity being monitored. The health model of a perishable commodity is generated using values of a plurality of parameters specific to the perishable commodity. During the health monitoring, all the parameters may not have to be measured. Instead, while establishing the correlation, values of all the parameters are estimated based on measured value of one or more other parameters. An example of health model is given in Table. 1.

TABLE 1

| Number | Temperature (degree Celsius) | Humidity ($R_H$) | RI | Ethylene rate (nl/g/hr) | $CO_2$ rate (ml/Kg/hr) | FI |
| --- | --- | --- | --- | --- | --- | --- |
| 1 | 20 | 80 | 7 | 3.8 | 48 | 2 |
| 2 | 25 | 75 | 7 | 3.96 | 51 | 1 |
| 3 | 18 | 85 | 7 | 3.5 | 54 | 3 |
| 4 | 18 | 95 | 7 | 3.43 | 57 | 4 |
| 5 | 20 | 80 | 1 | 0.75 | 30 | 6 |
| 6 | 25 | 75 | 1 | 1.5 | 40 | 4 |
| 7 | 18 | 85 | 1 | 0.5 | 28 | 7 |

Figure 5A:
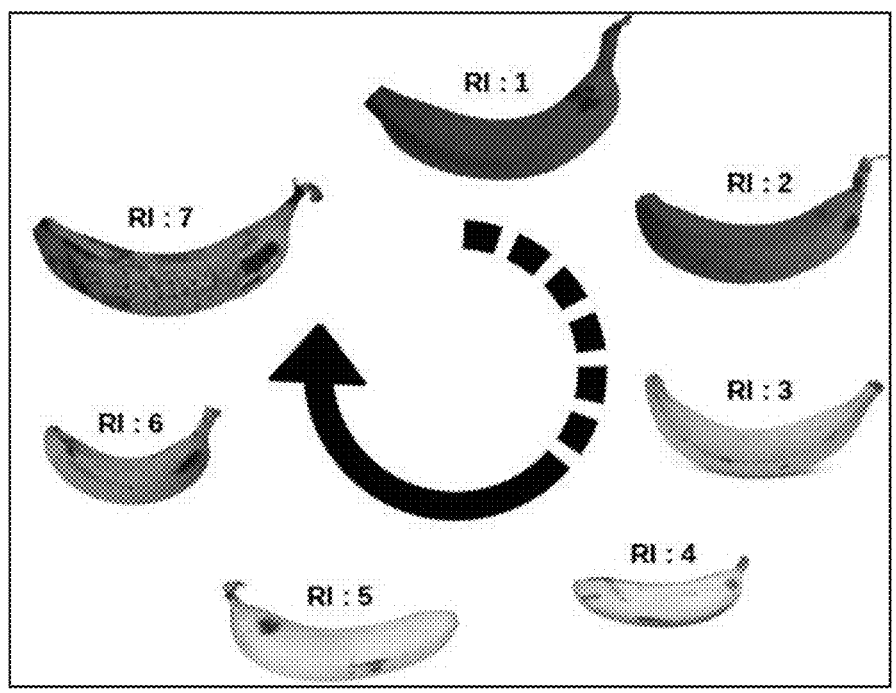
FIGS. 5A and 5B depict examples of health estimation of perishable commodities by the apparatus of FIG. 1, and corresponding correlation, in accordance with some embodiments of the present disclosure.

Further, based on the one or more time series images determined as having the correlation with the collected value of health parameters, health of the perishable commodity is determined. In an embodiment, the health of the perishable commodity is determined as a value belonging to a freshness index, wherein the freshness index includes a set of values, each value representing a particular health condition. For example, value '1' of degree of freshness may indicate that the perishable commodity being monitored is fresh while value '10' may indicate that the perishable commodity is not fresh/degrading. When the perishable commodity is a fruit as depicted in FIG. 5A, the apparatus 100 determines the 'degree of freshness' to indicate extent of ripening of the fruit, and in this scenario, a 'Ripening Index (RI)' also can be determined along with the Freshness Index, wherein value 1 of the RI indicates minimum ripening and value 10 indicates maximum ripening. As value of different parameters (for example amount of ethylene, CO2 and so on in the fruit) change with ripening condition of the fruit, there exists a correlation between RI of the fruit and values of different parameters/characteristic (ethylene rate in this example) of the fruit. Apart from health, amount of time left for the fruit to reach a particular degree of freshness also can be determined.

Out of the different RIs depicted in FIG. 5A, RI1 indicates that the fruit is hard, and RI7 may indicate that the fruit is ideal for consumption. For any fruit, when temperature is low and humidity is high, and when respiration rate is low, RI is less and the fruit is fresher and lasts longer. Hence Freshness index 10 indicates low freshness index as in the fruit should be consumed immediately and freshness index 7 indicates high freshness index which means banana will stay fresh for long and is not yet that ripe.

Example of an equation used for non-linear regression analysis for finding the freshness index is as follows:

$$\text{Freshness Index} = \theta_{0\_x0} + \theta_{1\_x1} + \theta_{2\_x2} + \theta_{3\_x3} + \theta_{4\_x1\_x2} + \theta_{5\_x2\_x3} + \theta_{6\_x3\_x1} \quad (1)$$

Where,
- $x_1$: Ripening Index
- $x_2$: $CO_2$ Rate
- $x_3$: Ethylene rate
- The $\theta$ parameter denotes the weightage factors of the respective features.

Equation (1) is given only as an example for the fruit health monitoring scenario. Such suitable equations are used in the health model for computing/estimating value of parameters for freshness monitoring. In the aforementioned example, correlation can be obtained with values of temperature and humidity alone, with an image of the fruit, and hence the freshness index can be determined without having to measure CO2 Rate or ethylene rate.

Figure 4:
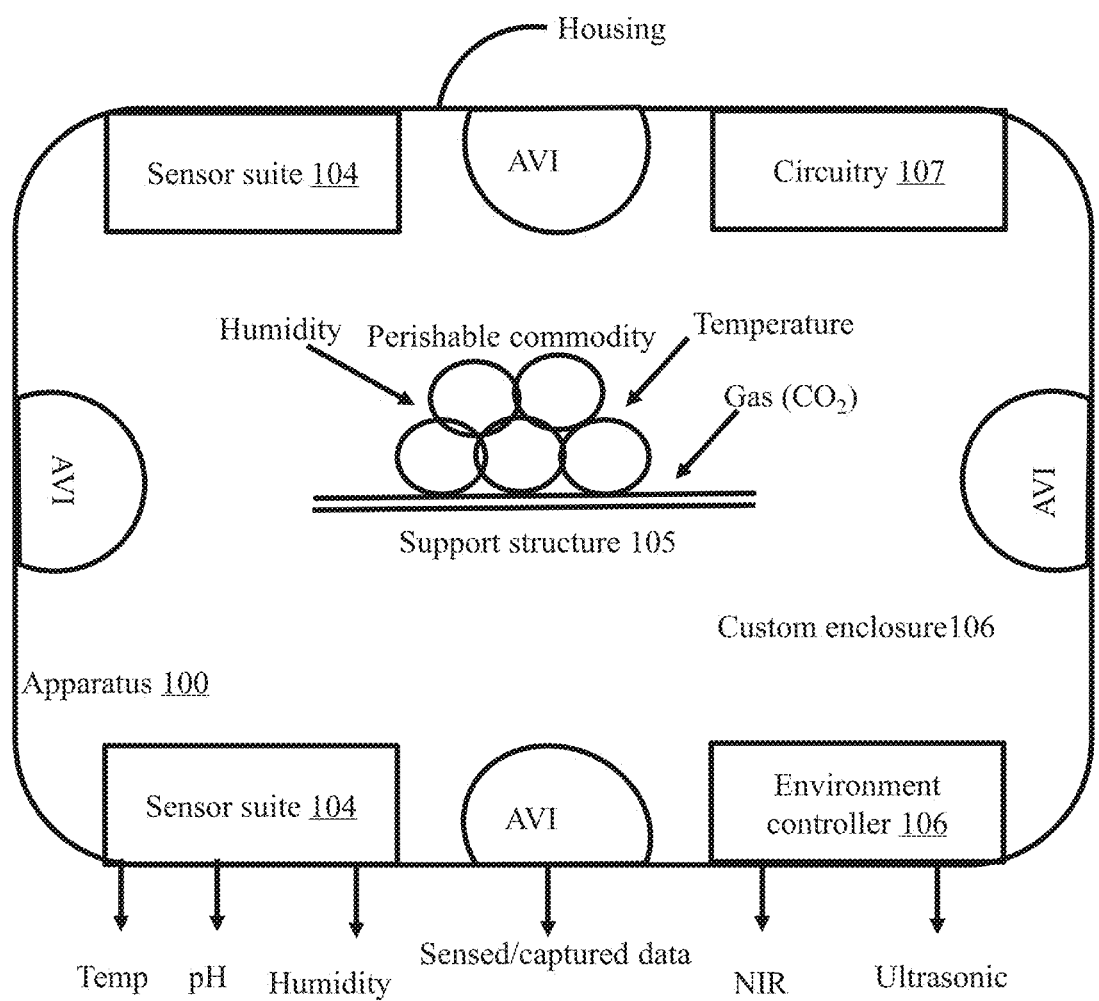
FIG. 4 depicts an exemplary implementation of the apparatus for monitoring the perishable commodity, using the apparatus of FIG. 1, in accordance with some embodiments of the present disclosure.
Figure 5B:
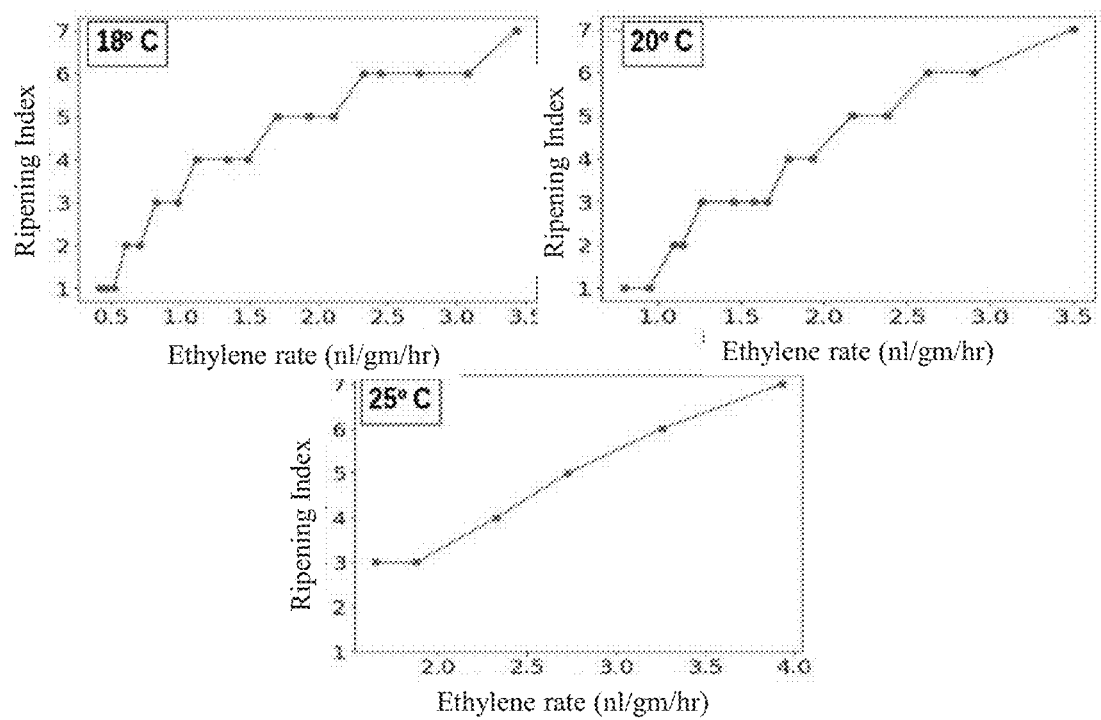

For example, in case of a supermarket, consider that temperature is 20 degree and humidity is 80. These values along with an image of the fruit when processed using the health model gives RI of 4, then calculated ethylene rate comes to be 2 nl/g/hr, and calculated CO2 rate comes to be 38 ml/Kg/hr. Once all these values are obtained, from the health model the freshness index is estimated as 3.5. Correlation of Ethylene and different RIs of the fruit under different temperature conditions are depicted in FIG. 5B. Further, an example implementation of the apparatus 100 is depicted in FIG. 4.

Figure 3:
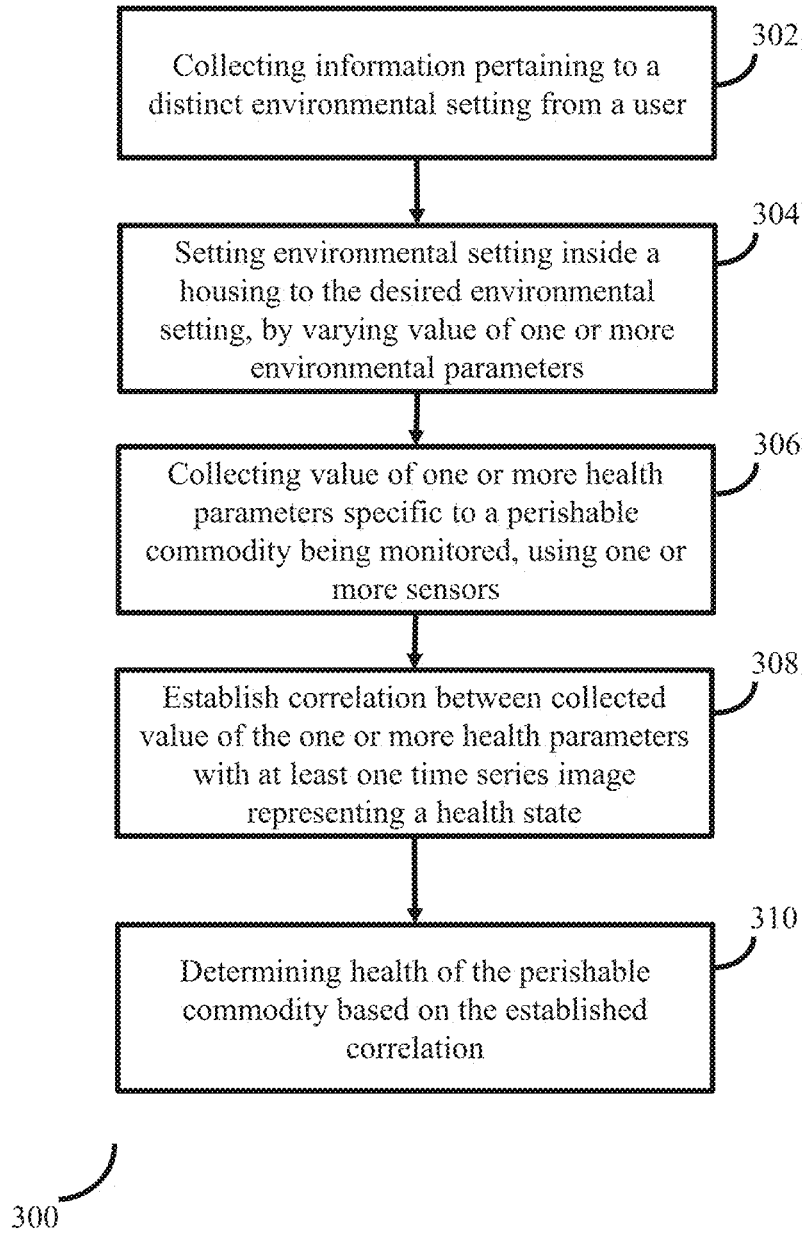
FIG. 3 is a flow diagram depicting steps involved in the process of monitoring health of the perishable commodity using the apparatus of FIG. 1, in accordance with some embodiments of the present disclosure.

FIG. 3 is a flow diagram depicting steps involved in the process of monitoring health of the perishable commodity using the apparatus of FIG. 1, in accordance with some embodiments of the present disclosure. Information pertaining to a distinct environmental setting is collected (302) as input through one or more user interfaces provided by the communication interface(s) 103, and accordingly sets (304) environmental setting inside the housing by changing value of one or more parameters.

Further, value of one or more health parameters specific to the perishable commodity being monitored is collected (306) and are further compared with a health model. By comparing the value of the health parameters with the health model, the apparatus 100 establishes a correlation between the collected value of parameters and at least one time series image representing a health state. Further, based on the established correlation, health of the perishable commodity is determined. In various embodiments, steps in method 300 may be performed in the same order as depicted in FIG. 3 or in any alternate order technically feasible. In an embodiment, one or more steps in the method 300 may be omitted.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope of the disclosed embodiments. Also, the words "comprising," "having," "containing," and "including," and other similar forms are intended to be equivalent in meaning and be open ended in that an item or items following any one of these words is not meant to be an exhaustive listing of such item or items, or meant to be limited to only the listed item or items. It must also be noted that as used herein and in the appended claims, the singular forms "a," "an," and "the" include plural references unless the context clearly dictates otherwise.

Furthermore, one or more computer-readable storage media may be utilized in implementing embodiments consistent with the present disclosure. A computer-readable storage medium refers to any type of physical memory on which information or data readable by a processor may be stored. Thus, a computer-readable storage medium may store instructions for execution by one or more processors, including instructions for causing the processor(s) to perform steps or stages consistent with the embodiments described herein. The term "computer-readable medium" should be understood to include tangible items and exclude carrier waves and transient signals, i.e., be non-transitory. Examples include random access memory (RAM), read-only memory (ROM), volatile memory, nonvolatile memory, hard drives, CD ROMs, DVDs, flash drives, disks, and any other known physical storage media.

It is intended that the disclosure and examples be considered as exemplary only, with a true scope of disclosed embodiments being indicated by the following claims.

What is claimed is:

1. An apparatus for monitoring health of a perishable commodity, comprising:
    a housing with closed walls;
    a sensor suite comprising a plurality of sensors, wherein the sensor suite is attached internally to the housing;
    a support structure for keeping the perishable commodity within the housing, wherein the perishable commodity is kept in proximity of the plurality of sensors;
    an environment controller for setting environment within the housing; and
    a circuitry configured within the housing and communicably coupled with the sensor suite to determine the health of the perishable commodity, the circuitry comprising:
    one or more hardware processors;
    one or more communication interfaces; and
    one or more memories storing a plurality of instructions, wherein the plurality of instructions when executed cause the one or more hardware processors to:
    collect information pertaining to a distinct environmental setting from a user;
    set the environment within a closed chamber to the distinct environmental setting by varying value of one or more environmental parameters;
    collect value of health parameters corresponding to the perishable commodity being monitored automatically based on inputs from a plurality of sensors and the plurality of sensors are selected automatically based on a type of perishable commodity being monitored and the health parameters to be measured, corresponding sensors for varied type of perishable commodities are pre-configured or dynamically configured in the memory;
    establish a correlation between the collected value of the health parameters with at least one time series image representing a health state, by comparing the collected value of the health parameters including temperature, humidity, amount of ethylene, CO2 rate, ethylene rate, freshness index (FI) with a pre-trained health model, the pre-trained health model trained on sensor and image data indicating change in health of a plurality of perishable commodities with time under plurality of environmental settings, wherein the health model is trained on a plurality of features extracted from a plurality of time series sensory data collected from the plurality of perishable commodities, wherein the time series sensory data is annotated as representing a degree of freshness level, wherein the health model is unique to each type of perishable commodity being monitored, and generated using values of the health parameters, wherein the freshness index includes a set of values, each value representing a particular health condition, value 1 of the freshness index indicate that the perishable commodity being monitored is fresh while value 10 indicate that the perishable commodity being monitored is degrading, wherein the degree of freshness level indicates varied stages with respect to freshness of the perishable commodity, wherein the varied stages include not ripen, medium ripen, fully ripen followed by determining a Ripening Index (RI) with values indicating minimum ripening and maximum ripening, and determine health of the perishable commodity based on the established correlation and determine amount of time left for the perishable commodity to reach a particular degree of freshness.

2. The apparatus as claimed in claim 1, wherein the health model is a combination of a plurality of machine learning algorithms.

3. The apparatus as claimed in claim 2, wherein the plurality of machine learning models comprise at least one Convolution Neural network (CNN) model, wherein the at least one CNN model is trained with a plurality of time series images to extract a plurality of vector representations which represent degradation in a plurality of perishable commodities, further wherein the vector representation of the time series images are annotated as representing a degree of freshness level.

4. The apparatus as claimed in claim 2, wherein the plurality of machine learning models comprise at least one Support Vector Regression (SVR) model.

5. A processor implemented method (300) for monitoring health of a perishable commodity using an apparatus (100), comprising:
collecting information pertaining to a distinct environmental setting from a user, via one or more hardware processors;
setting the environment within a closed chamber to the distinct environmental setting by varying value of the one or more environmental parameters, via the one or more hardware processors;
collecting value of health parameters corresponding to the perishable commodity being monitored automatically based on inputs, from a plurality of sensors and the plurality of sensors are selected automatically based on a type of perishable commodity being monitored and the health parameters to be measured, corresponding sensors for varied type of perishable commodities are pre-configured or dynamically configured in a memory, via the one or more hardware processors;
establishing a correlation between the collected value of the health parameters with at least one time series image representing a health state, by comparing the collected value of health parameters including temperature, humidity, amount of ethylene, $CO_2$ rate, ethylene rate, freshness index (FI) with a pre-trained health model, the pre-trained health model trained on sensor and image data indicating change in health of a plurality of perishable commodities with time under plurality of environmental settings, wherein the health model is trained on a plurality of features extracted from a plurality of time series sensory data collected from the plurality of perishable commodities, wherein the time series sensory data is annotated as representing a degree of freshness level, via the one or more hardware processors, wherein the health model is unique to each type of perishable commodity being monitored, and generated using values of the health parameters, wherein the freshness index includes a set of values, each value representing a particular health condition, value 1 of the freshness index indicate that the perishable commodity being monitored is fresh while value 10 indicate that the perishable commodity being monitored is degrading, wherein the degree of freshness level indicates varied stages with respect to freshness of the perishable commodity, wherein the varied stages include not ripen, medium ripen, fully ripen followed by determining a Ripening Index (RI) with values indicating minimum ripening and maximum ripening, and determining health of the perishable commodity based on the established correlation and determine amount of time left for the perishable commodity to reach a particular degree of freshness.

6. The method as claimed in claim 5, wherein the health model is a combination of a plurality of machine learning algorithms.

7. The method as claimed in claim 6, wherein the wherein the plurality of machine learning models comprise at least one Convolution Neural network (CNN) model, wherein the at least one CNN model is trained with a plurality of time series images to extract a plurality of vector representations which represent degradation in a plurality of perishable commodities, further wherein the vector representation of the time series images are annotated as representing a degree of freshness level.

8. The method as claimed in claim 6, wherein the plurality of machine learning models comprise at least one Support Vector Regression (SVR) model.

9. One or more non-transitory machine readable mediums comprising one or more instructions which when executed by one or more hardware processors for monitoring health of a perishable commodity using an apparatus (100), causes:
collecting information pertaining to a distinct environmental setting from a user;
setting the environment within a closed chamber to the distinct environmental setting by varying value of the one or more environmental parameters;
collecting value of health parameters corresponding to the perishable commodity being monitored automatically based on inputs, from a plurality of sensors and the plurality of sensors are selected automatically based on a type of perishable commodity being monitored and the health parameters to be measured, corresponding sensors for varied type of perishable commodities are pre-configured or dynamically configured in a memory;
establishing a correlation between the collected value of the health parameters including temperature, humidity, amount of ethylene, $CO_2$ rate, ethylene rate, freshness index (FI) with at least one time series image representing a health state, by comparing the collected value of health parameters with a pre-trained health model, the pre-trained health model trained on sensor and image data indicating change in health of a plurality of perishable commodities with time under plurality of environmental settings, wherein the health model is trained on a plurality of features extracted from a plurality of time series sensory data collected from the plurality of perishable commodities, wherein the time series sensory data is annotated as representing a degree of freshness level, wherein the health model is unique to each type of perishable commodity being monitored, and generated using values of the health parameters, wherein the freshness index includes a set of values, each value representing a particular health condition, value 1 of the freshness index indicate that the perishable commodity being monitored is fresh while value 10 indicate that the perishable commodity being monitored is degrading, wherein the degree of freshness level indicates varied stages with respect to freshness of the perishable commodity, wherein the varied stages include not ripen, medium ripen, fully ripen followed by determining a Ripening Index (RI) with values indicating minimum ripening and maximum ripening, and determining health of the perishable commodity based on the established correlation and determine amount of time left for the perishable commodity to reach a particular degree of freshness.

10. The one or more non-transitory machine readable mediums as claimed in claim 9, wherein the health model is a combination of a plurality of machine learning algorithms.

11. The one or more non-transitory machine readable mediums as claimed in claim 10, wherein the plurality of machine learning models comprise at least one Convolution Neural network (CNN) model, wherein the at least one CNN model is trained with a plurality of time series images to extract a plurality of vector representations which represent degradation in a plurality of perishable commodities, further wherein the vector representation of the time series images are annotated as representing a degree of freshness level.

12. The one or more non-transitory machine readable mediums as claimed in claim 10, wherein the plurality of machine learning models comprise at least one Support Vector Regression (SVR) model.

* * * * *